United States Patent [19]

Otsuka

[11] Patent Number: 5,523,027

[45] Date of Patent: Jun. 4, 1996

[54] LONG-WAVELENGTH UV LIGHT ABSORBER

[75] Inventor: Masahiro Otsuka, Osaka, Japan

[73] Assignee: Orient Chemical Industries, Ltd., Osaka-fu, Japan

[21] Appl. No.: 296,473

[22] Filed: Aug. 26, 1994

[30]  Foreign Application Priority Data

Aug. 27, 1993 [JP] Japan ................................ 5-212644

[51] Int. Cl.⁶ .................................................... F21V 9/04
[52] U.S. Cl. ............................................ 252/589; 546/153
[58] Field of Search .................................. 252/589, 582; 546/153

[56]  References Cited

U.S. PATENT DOCUMENTS

| | | | |
|---|---|---|---|
| 3,974,149 | 8/1976 | L'Eplattenier | 546/153 |
| 4,008,225 | 2/1977 | L'Eplattenier | 546/153 |
| 4,024,132 | 5/1977 | L'Eplattenier | 546/153 |
| 4,085,062 | 4/1978 | Virgilio et al. | |

FOREIGN PATENT DOCUMENTS 491280  6/1992  European Pat. Off. .

2442315  3/1975  Germany .

OTHER PUBLICATIONS

Chemical Abstracts, vol. 84, No. 22, 31 May 1976, Columbus, Ohio, US; abstract No. 155516f, JP-A-75 159 483.

Primary Examiner—Philip Tucker
Attorney, Agent, or Firm—Birch, Stewart, Kolasch & Birch

[57]  ABSTRACT

The present invention provides a UV light absorber comprising an azomethine compound represented by the formula:

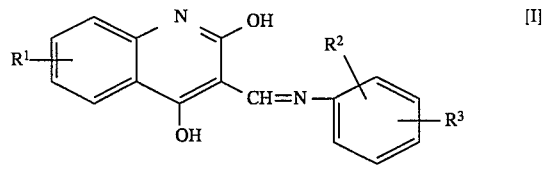

wherein $R^1$ is a hydrogen atom, or a straight- or branched-chain alkyl group having 1 to 4 carbon atoms; and $R^2$ and $R^3$ independently represent a hydrogen atom, a carboxyl group, a halogen atom, an alkoxy group having 1 to 4 carbon atoms, a straight- or branched-chain alkyl group having 1 to 12 carbon atoms or an alkoxycarbonyl group having 2 to 5 carbon atoms as an active ingredient.

13 Claims, 2 Drawing Sheets

LONG-WAVELENGTH UV LIGHT ABSORBER

FIELD OF THE INVENTION

The present invention relates to a UV light absorber. More particularly, it relates to a UV light absorber which absorbs long-wavelength UV light (UV-A) having a wavelength of 320 to 400 nm.

BACKGROUND OF THE INVENTION

UV light from the sun has a wavelength within a range of 240 to 400 nm. UV light is classified into three zones by the wavelength range. That is, they are UV light (UV-A) having a long wavelength of 320 to 400 nm which is referred to as a suntan wavelength, UV light (UV-B) having a wavelength of 280 to 320 nm which is referred to as a sunburn wavelength and UV light (UV-C) having a low wavelength of 240 to 280 nm which is absorbed in the ozone layer over the earth and scarcely reach the surface of the earth. Since a lot of organic compounds exposed to these radiations are decomposed or rendered unstable, UV light has hitherto been the factor which deteriorates the value of various commercial products.

UV light absorbers have been added to polymeric materials (e.g. plastic, rubber, etc.), heat-sensitive recording sheets and inks for heat transfer or liquid crystal display materials in order to provide light-resistant (weather-resistant) materials which have resistance to fading due to sunlight. Further, they have been used for cosmetics, paints, lens, filters, films, etc., in order to prevent inflammation of the human body as well as deterioration of products due to UV light.

As the UV light absorbers, for example, there have hitherto been known compounds such as salicylate, benzophenone, benzotriazole, cyanoacrylate, hydantoin derivative and hindered amine (photostabilizer) and the like.

Since most of them absorb UV light having a wavelength of 290 to 380 nm, they are transparent and have no substantial influence on transparency of plastics or colored products. However, they have an insufficient absorptivity to UV light having a wavelength within a range of 360 to 400 nm.

SUMMARY OF THE INVENTION

The main object of the present invention is to provide a UV light absorber which exhibits absorption with a large molecular absorption coefficient ε to UV-A, particularly UV light having a wavelength within a range of 360 to 400 nm, and a process for producing the same.

This object as well as other objects and advantages of the present invention will become apparent to those skilled in the art from the following description with reference to the accompanying drawings.

DETAILED DESCRIPTION OF THE INVENTION

Figure 1:
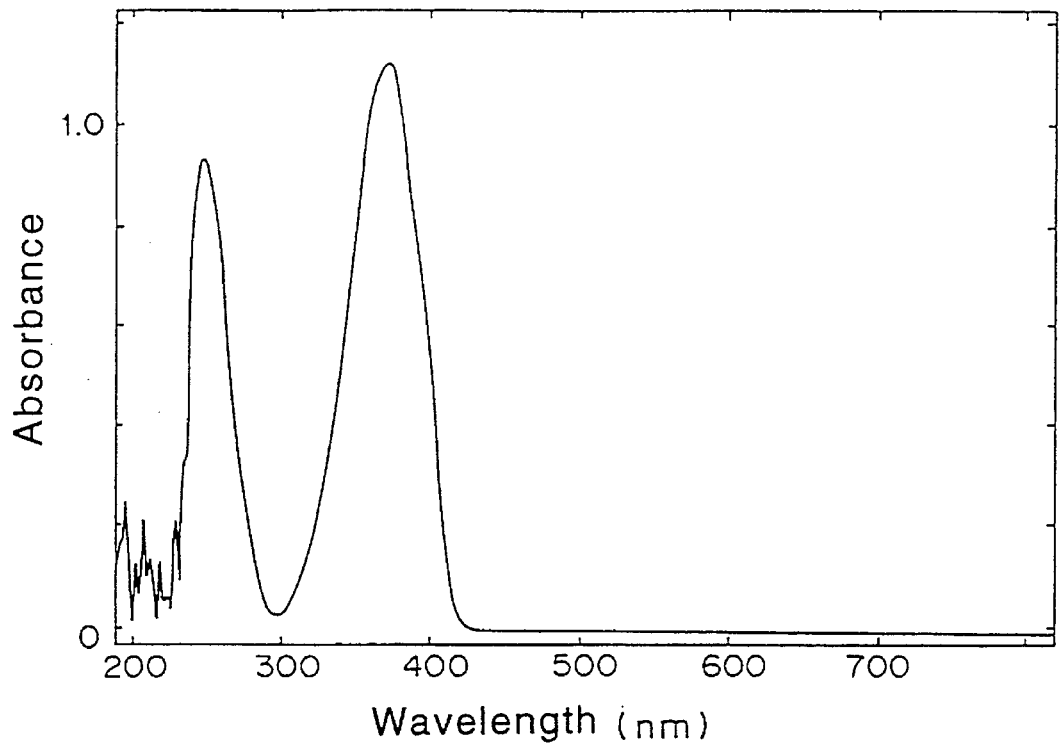
FIG. 1 is a near UV-visible spectrum of compound 1 which is a UV light absorber of the present invention.

The present invention provides a UV light absorber comprising an azomethine compound represented by the formula:

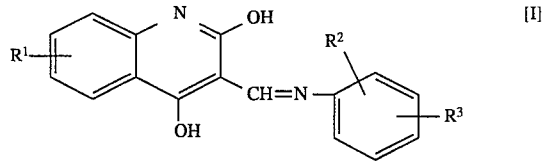

wherein $R^1$ is a hydrogen atom, or a straight- or branched-chain alkyl group having 1 to 4 carbon atoms (e.g. a methyl, ethyl, propyl, isopropyl, n-butyl and sec-butyl group); and $R^2$ and $R^3$ independently represent a hydrogen atom, a carboxyl group, a halogen atom (e.g. chlorine and bromine), an alkoxy group having 1 to 4 carbon atoms (e.g. a methoxy, ethoxy, propoxy and butoxy group), a straight- or branched-chain alkyl group having 1 to 12 carbon atoms (e.g. a lower alkyl group such as a methyl, ethyl, propyl, isopropyl, n-butyl and sec-butyl group, and a long-chain alkyl group such as an octyl and dodecyl group) or an alkoxycarbonyl group having 2 to 5 carbon atoms (e.g. alkyl ester group such as —COOCH$_3$, —COOC$_2$H$_5$, —COOC$_3$H$_7$ and —COOC$_4$H$_9$) as an active ingredient.

Preferably, the UV light absorber of the present invention may be produced by a step of reacting a 2,4,-dihydroxyquinoline derivative represented by the formula:

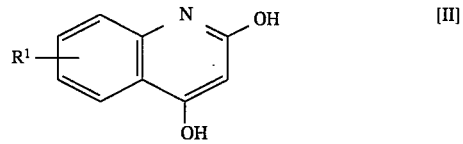

wherein $R^1$ is the same as defined above with a N,N'-di(phenyl)formamidine derivative represented by the formula:

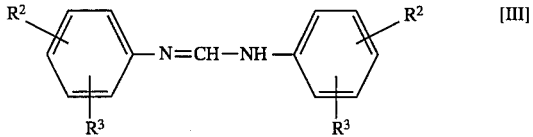

wherein $R^2$ and $R^3$ are the same as defined above or a compound represented by the formula:

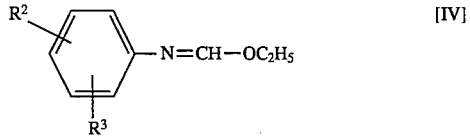

wherein $R^2$ and $R^3$ are the same as defined above by heating in an organic solvent.

As the 2,4-dihydroxyquinoline (derivative) which is used as the raw material in producing the present UV light absorber, for example, there are commercially available 2,4-dihydroxyquinolines, e.g. alkyl-substituted 2,4-dihydroxyquinoline such as 5-methyl-2,4-dihydroxyquinoline.

Examples of the N,N'-di(phenyl)formamidine derivative which is reacted with the 2,4-dihydroxyquinoline derivative include aromatic N,N'-bisformamidine compounds described in Japanese Patent Kokoku Publication No. 61-9993. In the present invention, it is particularly preferred to use N,N'-di(phenyl)formamidine, N,N'-di(3-methylphenyl)formamidine, formamidine, N,N'-di(3-N,N'-di(3-methoxyphenyl)formamidine, N,N'-di(4-ethoxyphenyl)formamidine, N,N'-di(3-chlorophenyl) formamidine, N,N'-di(4-carboxyphenyl)formamidine, N,N'-di(4-ethoxycarbonylphenyl)formamidine, N,N'-di(2,4-dimethylphenyl)formamidine, N,N'-di(2-methyl-5chlorophenyl)formamidine, N,N'-di(4-sec-butylphenyl) formamidine, and compounds represented by the formulas:

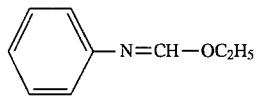

and

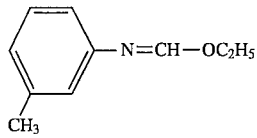

and the like.

The organic solvent is not specifically limited, and may be any one which can dissolve the raw materials to be used and compatible with them. It is preferred to use a solvent having high boiling point, because such a solvent is easy to raise a reaction temperature to complete the reaction. Examples of the organic solvent include glycols such as ethylene glycol, diethylene glycol, propylene glycol, etc., and dimethylformamide (DMF).

The reaction can be conducted by the procedure known to those skilled in the art. For example, a N,N'-di(phenyl)formamidine derivative and a 2,4-dihydroxyquinoline derivative are dissolved in a reaction vessel containing an organic solvent and then the mixture was reacted with stirring at a temperature of 130 to 200° C. for 0.5 to 2 hours.

The UV light absorber of the present invention can also be synthesized by a known method. For example, in DE-A-2,728,863, there is described a process for producing an azomethine compound as an intermediate of a metal complex dye, which comprises reacting a quinoline derivative obtained by formylation of a 2,4-dihydroxyquinoline (derivative), which is represented by the formula:

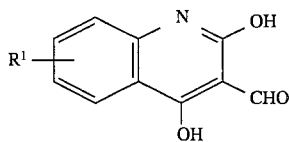

[V]

wherein $R^1$ is the same as defined above with aniline or nuclear substituted-aniline represented by the formula:

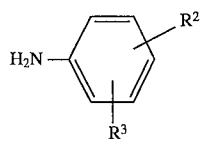

[VI]

wherein $R^2$ and $R^3$ are the same as defined above in alcohol under reflux.

Examples of the quinoline derivatives preferred for this method include 2,4-dihydroxy-3-formylquinoline and 3-formyl- 2,4-dihydroxy-5-methylquinoline.

On the other hand, examples of aniline or nuclear substituted-aniline which is condensed with the quinoline derivative include aniline, o-, m- and p-toluidine, o-, m- and p-xylidine, o-, m- and p-ethylaniline, p-(n-propyl) aniline, p-(tert-butyl)aniline, p-(sec-butyl)aniline, p-dodecylaniline, o-, m- and p-anisidine, o-, m- and p-phenetidine, monochloroaniline and the like.

This method has an advantage that the reaction can be conducted in a low boiling point alcoholic solvent. However, it is necessary to synthesize aldehyde by formylating 2,4-dihydroxyquinoline, and yield is low in comparison with the method of the present invention. Therefore, the conventional synthetic method is not advantageous compared to the present invention.

Examples of the UV light absorber represented by the formula [I] of the present invention thus obtained are shown in Table 1.

TABLE 1

| | | | λ max(nm) of UV light absorption spectra | | |
|---|---|---|---|---|---|
| $R^1$ | $R^2$ | $R^3$ | UV-C | UV-A | ε |
| 1 H | H | H | 254 | 378 | 30800 |
| 2 H | H | 3-CH$_3$ | 254 | 382 | 31200 |
| 3 H | H | 4-n-C$_3$H$_7$ | 254 | 384 | 30900 |
| 4 H | H | 3-OCH$_3$ | 258 | 370 | 25000 |
| 5 H | H | 4-OC$_2$H$_5$ | 254 | 388 | 29200 |
| 6 H | H | 3-Cl | 254 | 378 | (31900) |
| 7 H | H | 4-COOC$_2$H$_5$ | 270 | 384 | (27000) |
| 8 H | 2-CH$_3$ | 4-CH$_3$ | 254 | 382 | 29600 |
| 9 H | 2-CH$_3$ | 5-Cl | 256 | 384 | 29000 |
| 10 H | H | 4-sec-C$_4$H$_9$ | 254 | 384 | 29500 |
| 11 5-CH$_3$ | H | H | 254 | 378 | 30600 |

In Table 1, λ max is a maximum value of UV light absorption spectra measured by using chloroform as a solvent and ε is a molecular absorption coefficient at a UV-A maximum absorption wavelength measured in a chloroform solvent. Incidentally, ε in parentheses means a value measured by dissolving a sample in dimethylformamide, followed by diluting with chloroform.

Further, the commercially available UV light absorber is described in Coloring Material, 65 (5), pages 298–307, 1992, "The Present Development State of The UV Light Absorber", Tomomi OKAZAKI. Examples thereof are shown in Table 2.

TABLE 2

| Name of compound | Appearance | Molecular weight | Effective wavelength |
|---|---|---|---|
| 2-(2-Hydroxy-5-methylphenyl)benzotriazole | Pale yellow | 225 | 270–370 |
| 2-(3,5-di-t-amyl-2-hydroxyphenyl)benzotriazole (TINUVIN 328) | Pale yellow | 351 | 270–380 |
| 2,4-Dihydroxybenzophenone | Pale yellow | 326 | 280–340 |
| Ethyl-2-cyano-3,3'-diphenyl acrylate (UVINUL N35) | White | 277 | 270–350 |
| P-tert-butylphenyl salicylate | White | 270 | 290–330 |
| Dibenzoylmethane derivative | — | — | UV-A |

In general, the UV light absorber of the present invention exhibits good dispersibility or solubility to solvents, resins, waxes, etc., which are used for various applications of UV light absorption. Further, it has excellent resistance against various organic substances, light and heat. Accordingly, the 2,4-dihydroxyquinoline derivative represented by the formula [I] of the present invention can suitably be used for resin compositions for various applications.

The UV light absorber of the present invention is used in the form of powder, dispersion or solution in water and in organic solvent, or resin solution.

As the solvent in which the UV light absorber of the present invention is finely dispersed or dissolved, for example, there are hydrocarbons such as toluene, xylene, cyclohexane, etc.; halogenated hydrocarbons such as methylene chloride, ethylene chloride, etc.; alcohols such as methanol, ethanol, etc.; cellosolves such as ethylene glycol monoethyl ether, etc.; esters such as ethyl acetate, etc.; ketones such as methyl ethyl ketone, methyl isobutyl ketone, etc. These solvents are used alone or in combination thereof for various applications such as paints.

Examples of the resin which can use the UV light absorber of the present invention include resins for coating (e.g. thermoplastic resins such as acrylic, vinyl chloride, polyolefin, polyester and polyamide, and thermosetting resins such as phenolic, epoxy and polyester), reins for film forming (e.g. natural resins such as a cellulose acetate derivative, an ethylene oxide resin, a butyral resin, a vinyl resin, an alkyd resin and a phenol resin), binder resins for heat transfer (e.g. polyvinyl butyral, ethylhydroxyethyl cellulose, styrene-maleic anhydride copolymer, a methyl methacrylate resin, a polyester resin and wax), binder resins of toner for electrophotography a styrene resin, a styrene-acrylic resin, a styrene-butadiene resin, a styrene-vinyl methyl ether resin and polyester), acrylic resins for plastic lens, polycarbonates, allyl diglycol carbonate resins, plastics for molding, resins for plastic film and the like. The UV light absorber of the present invention can also be suitably used for polymer liquid crystals, in addition to the above resins.

When formulating the UV light absorber of the present invention in the above compositions for various applications, the formulating amount is not specifically limited, and may be the amount which is enough to stabilize the composition to the predetermined extent. The UV light absorber of the present invention can be normally used in the amount of 0.001 to 5%, preferably about 2% or less, based on the amount of the solid content of the organic substance. When the amount of the UV light absorber exceeds the suitable range, visible light transmittance and transparency may be deteriorated.

When a dyeable plastic substrate is dyed by a dipping method, it is considered to be a surface dyeing, and therefore, the concentration of the dye based on the total resin is substantially not more than 0.001%. The present UV light absorber provides sufficient effect even if it is used in such a small amount. On the other hand, when the amount exceeds 5% by weight, dispersibility of the UV light absorber as well as color tone of an organic colored substance or a resin composition may be deteriorated, and therefore, it is not preferred. Further, even if the UV light absorber is added in an amount of more than 5% by weight, the resulting absorptive effect is not much different from that obtained by adding the suitable amount of the absorber, the practical cost becomes high, and therefore, it is not preferred.

The UV light absorber of the present invention can be used in combination with a UV light absorbers for UV-B (e.g. those shown in Table 2), which have hitherto been known, without causing harmful effect. Further, fluorescent brighteners, radical scavengers, etc. can be added to the UV light absorber of the present invention depending on the application and object.

As described above, the UV light absorber of the present invention has a maximum absorption wavelength within a UV light range of UV-A and UV-C, and is stable against various organic substance as well as light and heat. In addition, the UV light absorber of the present invention exhibits high UV light absorptive effect because a molecular absorption coefficient $\epsilon$ at the maximum absorption wavelength ($\lambda$ max) of UV-A exceeds $2.5 \times 10^4$.

The UV light absorber of the present invention absorbs UV light within a long-wavelength UV light range, at which a suitable UV light absorber has not hitherto been found, and has good compatibility with various organic substances. Accordingly, in order to protect the organic substance from the influence of long-wavelength UV light and to prevent fading of a colored article, the UV light absorber of the present invention can be used for molded plastic article such as sunglass, resin film, UV light cut-off filter, film-forming material such as paint, material for liquid crystal display, ink for heat transfer and printing, electrophotographic toner and the like.

The following Examples further illustrate the present invention in detail but are not to be construed to limit the scope thereof.

In Examples 1 to 11, synthesis of the UV light absorber of the present invention will be explained.

EXAMPLE 1

(Synthesis of compound 1 shown in Table 1)

To 100 ml of ethylene glycol, 16.1 g of 2,4-dihydroxyquinoline and 21.6 g of N,N'-di(phenyl)formamidine were added and the mixture was maintained at 170 to 175° C. for 30 minutes with stirring. The mixture was air-cooled with stirring, and 100 ml of methyl ethyl ketone as a diluent solvent was added dropwise at 120° C. After the mixture was filtered at 60° C., the resulting cake was washed with methyl ethyl ketone and dried to give 24.5 g of a pale yellow powder. The yield was 92.8%. Further, the melting point was measured using a Metler thermosystem FP900. As a result, the melting point was m.p. 262 to 265° C. A near UV-visible spectrum of the resulting compound is shown in FIG. 1.

EXAMPLE 2

(Synthesis of compound 2 shown in Table 1)

To 100 ml of ethylene glycol, 16.1 g of 2,4-dihydroxyquinoline and 22.5 g of N,N'-di(3-methylphenyl) formamidine were added and the mixture was maintained at 170 to 175° C. for 30 minutes with stirring. The mixture was air-cooled with stirring, and 100 ml of ethanol as a diluent solvent was added dropwise at 120° C. After the mixture was filtered at 60° C., the resulting cake was washed with ethanol and dried to give a pale yellow powder, m.p. 236 to 240° C. The yield was 88.0%

EXAMPLES 3 to 10

(Synthesis of compounds 3 to 10 shown in Table 1)

According to the same manner as that described in Example 1 except for using N,N'-di(4-n-propylphenyl) formamidine, N,N'-di(4-methoxyphenyl)formamidine, N,N'-di(4-ethoxyphenyl)formamidine, N,N'-di(3-chlorophenyl) formamidine, N,N'-di(4-ethoxycarbonylphenyl)formamidine, N,N'-di(2,4-dimethylphenyl)formamidine, N,N'-di(2-methyl-5-chlorophenyl)formamidine or N,N'-di(4-sec-butylphenyl) formamidine instead of N,N'-di(phenyl)formamidine, a UV light absorber powder was produced, respectively.

EXAMPLE 11

According to the same manner as that described in Example 2 except for using 5-methyl-2,4-dihydroxyquinoline and a compound ($C_6H_5$—N=CH—O—$C_2H_5$), respectively, instead of 2,4-dihydroxyquinoline and N,N'-di(3-methylphenyl) formamidine, a UV light absorber powder was produced.

COMPARATIVE EXAMPLE 1

(Synthesis of compound 1 shown in Table 1 by a conventional method)

To 100 ml of ethanol, 2,4-dihydroxy-3-formylquinoline obtained by formylation of 16.1 g of 2,4-dihydroxyquinoline and 9.5 g of aniline were added and the mixture was maintained under reflux for 180 minutes. The mixture was air-cooled with stirring and filtered at room temperature. Then, the resulting cake was washed with ethanol, dried and then recrystallized from dimethylformamide (DMF) to give a pale yellow powder, m.p. 262 to 265° C. The yield was about 55%. The powder was subjected to a spectrum analysis. As a result, an absorption curve which is the same as that of Example 1 was obtained.

In Examples A to F, the use of the UV light absorber of the present invention will be explained.

EXAMPLE A (Plastic lens)

To acryldiglycol carbonate (CR-39, manufactured by Tokuyama Soda Co., Ltd.) as a monomer for corrective lens, the compound 1 as the UV light absorber of the present invention was added in an amount of 0.008% by weight based on a total amount of the monomer. The resulting mixture was molten and was polymerized/molded by a cast molding method to obtain a transparent polymerized plate A having a thickness of 2.5 mm.

Further, a commercially available benzophenone UV light absorber [TINUVIN 328 (trade name), manufactured by Ciba Geigy Co.] was added to a monomer in an amount of 0.15% by weight based on a total amount of the monomer to prepare a similar polymerized plate (comparative sample A) for comparison. Transmittance at 400 nm of the respective polymerized plates was measured, respectively. As a result, transmittance of the sample A was 0% and that of the comparative sample A was 76%. Thus, it was confirmed that the UV light absorber of the present invention is superior in absorption characteristics at around 400 nm.

EXAMPLE B

The monomer (CR-39) used in Example A was subjected to cast polymerization to obtain a transparent polymerized plate having a thickness of 1.5 mm.

The polymerized plate was subjected to a coating treatment by dipping in a film-forming solution, in which 4 g of the compound 1, 4 g of TWEEN 20 (manufactured by Kao Atlas Co., Ltd.) as a dispersant and 0.1 g of methyl salicylate were dispersed/dissolved in 1000 ml of water, at 95° C. for 5 and 20 minutes to obtain samples B5 and B20, respectively. Transmittance at 400 nm of the respective samples thus obtained was measured, respectively. The measurement results are shown in Table 3.

Then, according to the same manner as that described in Example B except for substituting a commercially available TINUVIN 328 for the compound 1, comparative samples CB5 and CB20 were prepared and transmittance at 400 nm was measured, respectively. The measurement results are shown in Table 3.

EXAMPLE C

According to the same manner as that described in Example A except for substituting a monomer (PC) having a refractive index of 1.6 for the monomer (CR-39), the mixture was subjected to cast polymerization to obtain a transparent polymerized plate having a thickness of 1.5 mm.

The polymerized plate was subjected to a coating treatment by dipping in a film-forming solution, in which 2 g of the compound 1 and 2 g of TWEEN 20 as a dispersant were dispersed/dissolved in 1000 ml of water, at 95° C. for 30 and 60 minutes to obtain samples C30 and C60, respectively.

Then, according to the same manner as that described in Example C except for substituting a commercially available TINUVIN 328 for the compound 1, comparative samples CC30 and CC60 were prepared and transmittance at 400 nm was measured, respectively. The measurement results are shown in Table 3.

EXAMPLE D

According to the same manner as that described in Example C except for using a film-forming solution composed of 1 g of the compound 1, 1 g of TINUVIN 328, 2 g of TWEEN and 1000 ml of water, samples D30 and D60 were prepared, respectively.

Transmittance at 400 nm of the respective samples was measured, respectively. The measurement results are shown in Table 3.

TABLE 3

| Example No. | Sample No. | Dipping time (minute) | Transmittance (%) |
| --- | --- | --- | --- |
| Example B | B5 | 5 | 14.2 |
|  | B20 | 20 | 4.9 |
| Example B | CB5 | 5 | 40.1 |
|  | CB20 | 20 | 23.3 |
| Example | CC30 | 30 | 4.9 |
|  | C60 | 60 | 2.1 |
| Example C | CC30 | 30 | 22.4 |
|  | CC60 | 60 | 14.4 |
| Example D | D30 | 30 | 1.5 |
|  | D60 | 60 | 0.5 |

A UV light absorption effect of the present invention is apparent from Examples A to D, and synergistic effect due to the combination with a conventional product was also remarkable. Regarding the other ultraviolet light absorber (e.g. compound 7) of the present invention, a similar effect was confirmed.

EXAMPLE E

| | |
| --- | --- |
| (UV light cut-off protective member) | 100 Parts |
| DIANAL LR-1065 (40% MEK solution of acrylic resin, manufactured by Mitsubishi Rayon Co., Ltd.) | |
| Compound 1 | 0.5 Parts |
| YUBINAL N35 | 1.0 Part |

A transparent paint of the above formulation was applied on a PET (polyethylene terephthalate) film having a thickness of 100 μm using a bar coater such that a dried coating have a thickness of about 30 μm, followed by drying to form a transfer layer on the PET film to obtain a transfer release type UV light cut-off protective member. Then, solid setting of magenta color was provided on a ink-jet recording paper using an ink-jet printer and the protective member prepared above was laminated thereon using a laminator such that the transfer layer covers the solid setting. Thereafter, the PET film was peeled off from the recorded surface to obtain a laminate sample A.

The laminate sample A and a comparative sample prepared according to the same manner as that described above except that the UV light cut-off protective member was not laminated were subjected to a light-resistance evaluation test. The light-resistance evaluation test was conducted by irradiating light in a UV light long-life fade-meter (carbon arc type) manufactured by Suga Co., Ltd. for 20 hours.

As a result, regarding the sample A, fading was scarcely observed at the magenta setting part before and after irradiation. Regarding the comparative sample, fading was observed clearly. It was confirmed by the above results that the UV light absorptive effect of the present invention is remarkable.

EXAMPLE F

Figure 2:
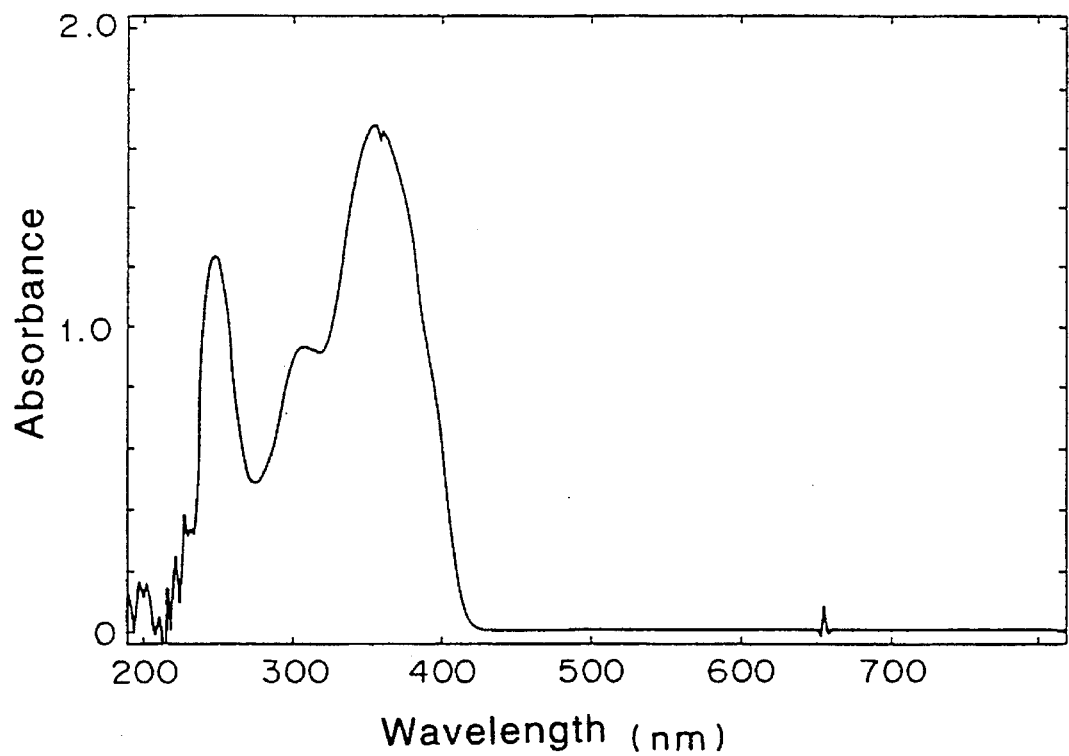
FIG. 2 is a near UV-visible spectrum obtained in the case that compound 1 is mixed with a benzotriazole UV light absorber in a proportion of 1:2.
Figure 3:
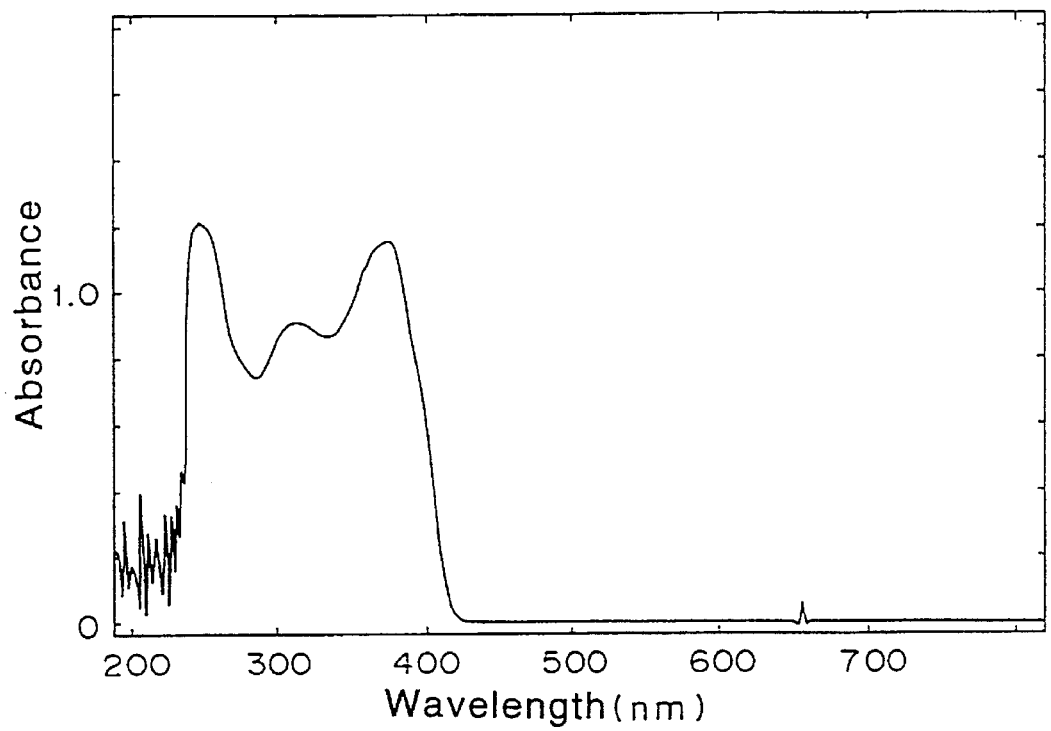
FIG. 3 is a near UV-visible spectrum obtained in the case that compound 1 is mixed with a cyanoacrylate UV light absorber in a proportion of 1:2.
Figure 4:
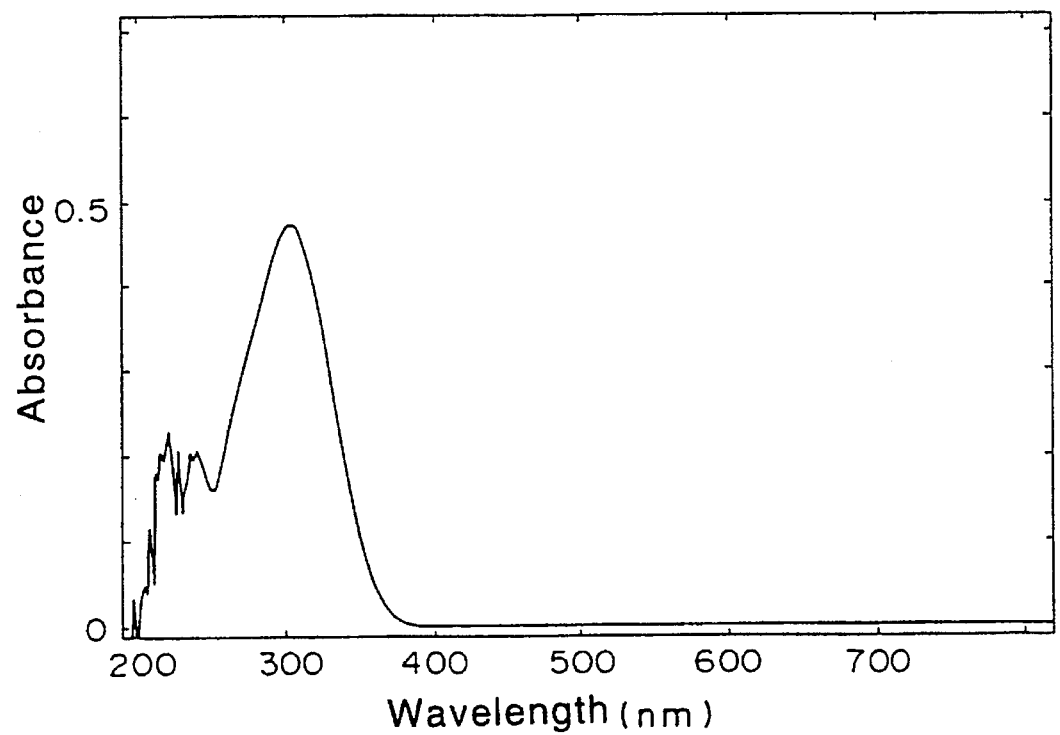
FIG. 4 is a near UV-Visible spectrum of a cyanoacrylate UV light absorber.

A near UV-visible spectrum of the compound I and that obtained in case that a commercially available UV light absorber is used in combination are shown in FIG. 2 and 3, respectively. FIG. 2 is a graph illustrating a near UV-visible spectrum obtained in case that the compound I of the present invention is mixed with TINUVIN 328 (benzotriazole UV light absorber) in the proportion of 1:2. FIG. 3 is a graph illustrating a near UV-visible spectrum obtained in case that the compound I of the present invention is mixed with UVINUL N35 (cyanoacrylate UV light absorber, manufactured by BASF Co.) in the proportion of 1:2. FIG. 4 is a graph illustrating a near UV-visible spectrum of UVINUL N35 alone.

As is apparent from FIGS. 2 and 3, the UV light absorber of the present invention transmits UV-B. Therefore, it was confirmed that the UV light absorber exhibits UV light absorption characteristics within a range of 250 to 400 nm when using a UV light absorber having maximum absorption at about 300 nm in combination.

What is claimed is:

1. A process for improving light-resistance of a molded resin material which comprises: adding a UV light absorber azomethine compound represented by the formula:

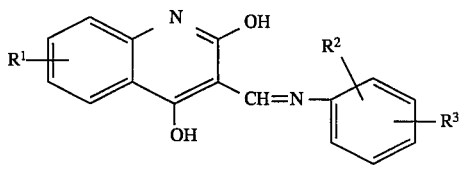

wherein $R^1$ is a hydrogen atom, or a straight- or branched-chain alkyl group having 1 to 4 carbon atoms; and $R^2$ and $R^3$ independently represent a hydrogen atom, a carboxyl group, a halogen atom, an alkoxy group having 1 to 4 carbon atoms, a straight- or branched-chain alkyl group having 1 to 12 carbon atoms or an alkoxycarbonyl group having 2 to 5 carbon atoms, to a settable resin composition; and molding and setting the resin composition.

2. The method according to claim 1, wherein the $R^1$ is selected from the group consisiting of a hydrogen atom and a methyl group.

3. The method according to claim 1, wherein the $R^2$ is selected from the group consisiting of a hydrogen atom and a methyl group.

4. The method according to claim 1, wherein the $R^3$ is selected from the group consisiting of a hydrogen atom, a chlorine atom, a methyl, n-propyl, sec-butyl, methoxy, ethoxy and ethoxycarbonyl group.

5. The process according to claim 1, wherein the UV light absorber is added in an amount of 0.001–5% by weight based on the solid content of the settable resin composition.

6. A molded resin material prepared by the process according to claim 1.

7. A molded resin material prepared by the process according to claim 5.

8. A UV light cut-off filter prepared by the process according to claim 1.

9. A coating composition, comprising a solvent and a UV-light absorber azomethine compound represented by the formula:

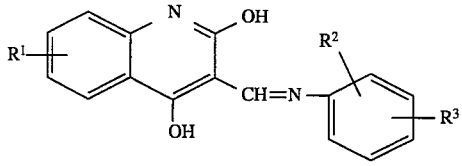

wherein $R^1$ is a hydrogen atom, or a straight- or branched-chain alkyl group having 1 to 4 carbon atoms; and $R^2$ and $R^3$ independently represent a hydrogen atom, a carboxyl group, a halogen atom, an alkoxy group having 1 to 4 carbon atoms, a straight- or branched-chain alkyl group having 1 to 12 carbon atoms or an alkoxycarbonyl group having 2 to 5 carbon atoms in an amount of 0.001–5% by weight based on the solid content of the coating composition.

10. The composition according to claim 9, wherein the $R^1$ is selected from the group consisting of a hydrogen atom and a methyl group.

11. The composition according to claim 9, wherein the $R^2$ is selected from the group consisting of a hydrogen atom and a methyl group.

12. The composition according to claim 9, wherein the $R^3$ is selected from the group consisting of a hydrogen atom, a chlorine atom, methyl, n-propyl, sec-butyl, methoxy, ethoxy, and ethoxycarbonyl group.

13. The composition according to claim 9, wherein said solvent is selected from the group consisting of water, hydrocarbons, halogenated hydrocarbons, alcohols, cellosolves, esters, and ketones.

* * * * *